(12) United States Patent
Gomer et al.

(10) Patent No.: US 11,699,220 B2
(45) Date of Patent: Jul. 11, 2023

(54) FUSION OF MOLECULAR CHEMICAL IMAGING WITH RGB IMAGING

(71) Applicant: CHEMIMAGE CORPORATION, Pittsburgh, PA (US)

(72) Inventors: Heather Gomer, Sewickley, PA (US); Patrick Treado, Pittsburgh, PA (US); Jihang Wang, Turtle Creek, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 0 days.

(21) Appl. No.: 17/061,686

(22) Filed: Oct. 2, 2020

(65) Prior Publication Data

US 2021/0104028 A1 Apr. 8, 2021

Related U.S. Application Data

(60) Provisional application No. 62/909,525, filed on Oct. 2, 2019.

(51) Int. Cl.
*G06T 5/50* (2006.01)
*H04N 5/265* (2006.01)
*G06T 5/00* (2006.01)
*G01N 33/483* (2006.01)
*H04N 23/56* (2023.01)
*H04N 23/80* (2023.01)
*H04N 23/90* (2023.01)
*A61B 5/00* (2006.01)

(52) U.S. Cl.
CPC ........... *G06T 5/50* (2013.01); *G01N 33/4833* (2013.01); *G06T 5/007* (2013.01); *H04N 5/265* (2013.01); *H04N 23/56* (2023.01); *H04N 23/80* (2023.01); *H04N 23/90* (2023.01); *A61B 5/0084* (2013.01); *G06T 2207/10024* (2013.01); *G06T 2207/10048* (2013.01); *G06T 2207/20221* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 5,555,324 A * | 9/1996 | Waxman | G06T 5/20 348/E5.09 |
| 2008/0095422 A1 | 4/2008 | Suri et al. | |
| 2008/0219654 A1 | 9/2008 | Border et al. | |
| 2011/0249323 A1 | 10/2011 | Tesar et al. | |
| 2012/0062697 A1 | 3/2012 | Treado et al. | |
| 2014/0043488 A1* | 2/2014 | Treado | G01J 3/027 348/164 |

(Continued)

OTHER PUBLICATIONS

Bayesian methods for image fusion, Jurgen Beyerer, 2008 (Year: 2008).*

(Continued)

*Primary Examiner* — James M Hannett
(74) *Attorney, Agent, or Firm* — DLA Piper LLP (US)

(57) ABSTRACT

Methods, systems, and computer program products of fusing Molecular Chemical Imaging (MCI) and Red Green Blue (RGB) images are disclosed herein. A sample is illuminated with illuminating photons which interact with the sample and are used to form MCI and RGB images. The MCI and RGB images are fused by way of mathematical operations to generate a RGB image with a detection overlay.

24 Claims, 2 Drawing Sheets

(56) References Cited

U.S. PATENT DOCUMENTS

| | | | |
|---|---|---|---|
| 2015/0018690 A1* | 1/2015 | Kang | A61B 5/418 |
| | | | 600/473 |
| 2015/0042816 A1 | 2/2015 | Karels et al. | |
| 2017/0367580 A1* | 12/2017 | DiMaio | A61B 5/0077 |
| 2019/0209000 A1* | 7/2019 | Treado | A61B 1/051 |
| 2019/0281781 A1* | 9/2019 | Borrowman | B07C 5/3425 |

OTHER PUBLICATIONS

Xu et al., "Adaptive Weighted Fusion: A Novel Fusion Approach for Image Classification," Neurocomputing 168; May 27, 2015, pp. 566-574.

* cited by examiner

FUSION OF MOLECULAR CHEMICAL IMAGING WITH RGB IMAGING

CROSS REFERENCE TO RELATED APPLICATIONS

This application claims priority to U.S. Provisional Application Ser. No. 62/909,525 filed on Oct. 2, 2019, the content of which is hereby incorporated by reference in its entirety.

FIELD OF DISCLOSURE

Although molecular chemical imaging (MCI) is a powerful technique for analyzing organic, inorganic, and biological samples of interest, it has drawbacks. One drawback is that many implementations do not achieve real-time or near real-time imaging because of limitations in the imaging hardware. Another drawback is that the MCI image that is generated can be difficult to interpret when used alone. This is especially important for biological or medical applications. There is a continued need to fuse the information from multiple images into a single image that includes greater information and contrast.

SUMMARY

The disclosure contemplates various embodiment of imaging techniques that fuse two or more images generated from samples of interest.

In one embodiment, there is a method of fusing images, the method comprising illuminating a sample with illuminating photons; obtaining a first sample image from interacted photons that have interacted with the sample and have traveled to a first camera chip; obtaining a second sample image from interacted photons that have interacted with the sample and have traveled to a second camera chip; and fusing the first sample image and the second sample image by weighting the first sample image and the second sample image, wherein the weighting of the first sample image and the second sample image is performed by one or more of Image Weighted Bayesian Fusion (IWBF), Partial Least Squares Discriminant Analysis (PLS-DA), linear regression, logistic regression, Support Vector Machines (SVM), Relative Vector Machines (RVM), Naïve Bayes, neural network, or Linear Discriminant Analysis (LDA), to thereby generate a fused score imag.

In another embodiment, the method also comprises detecting glare in each of the first sample image and the second sample image and not classifying the portions of the first sample image and the second sample image that are identified as glare.

In another embodiment, the method further comprises normalizing the intensities of the first sample image and the second sample image.

In another embodiment, the first sample image is selected from the group consisting of UV, RGB, Vis-NIR, SWIR, Raman, NIR-eSWIR, and eSWIR, and the second sample image is selected from the group consisting of UV, RGB, Vis-NIR, SWIR, Raman, NIR-eSWIR, and eSWIR.

In another embodiment, the first sample image is RGB, and the second sample image is Vis-NIR.

In another embodiment, the first sample image is RGB that is converted to Hue, Saturation, Value (HSV) and the Value dimension of the first sample image is omitted.

In another embodiment, the second sample image is Vis-NIR.

In one embodiment, there is a system for fusing images, the system comprising an illumination source configured to illuminate a sample with illuminating photons; a first camera chip configured to obtain a first sample image from interacted photons that have interacted with the sample; a second camera chip configured to obtain a second sample image from interacted photons that have interacted with the sample; and a processor that during operation fuses the first sample image and the second sample image by weighting the first sample image and the second sample image, wherein the weighting of the first sample image and the second sample image is performed by one or more of Image Weighted Bayesian Fusion (IWBF), Partial Least Squares Discriminant Analysis (PLS-DA), linear regression, logistic regression, Support Vector Machines (SVM), Relative Vector Machines (RVM), Naïve Bayes, neural network, or Linear Discriminant Analysis (LDA) to thereby generate a fused score image.

In another embodiment, the processor detects glare in each of the first sample image and the second sample image and does not classify the portions of the first sample image and the second sample image that are identified as glare.

In another embodiment, the processor normalizes the intensities of the first sample image and the second sample image.

In another embodiment, the first sample image is selected from the group consisting of UV, RGB, Vis-NIR, SWIR, Raman, NIR-eSWIR, and eSWIR, and the second sample image is selected from the group consisting of UV, RGB, Vis-NIR, SWIR, Raman, NIR-eSWIR, and eSWIR.

In another embodiment, the first sample image is RGB, and the second sample image is Vis-NIR.

In another embodiment, the first sample image is RGB and the processor converts the first sample image from RGB to Hue, Saturation, Value (HSV) and the processor omits the Value dimension of the first sample image.

In another embodiment, the second sample image is Vis-NIR.

In one embodiment, there is a computer program product for fusing images embodied by instructions on a non-transitory computer readable storage medium, which when the instructions are executed by a processor causes an illumination source to illuminate a sample with illuminating photons; a first camera chip to obtain a first sample image from interacted photons that have interacted with the sample; a second camera chip to obtain a second sample image from interacted photons that have interacted with the sample; and the processor to fuse the first sample image and the second sample image by weighting the first sample image and the second sample image, wherein the weighting of the first sample image and the second sample image is performed by one or more of Image Weighted Bayesian Fusion (IWBF), Partial Least Squares Discriminant Analysis (PLS-DA), linear regression, logistic regression, Support Vector Machines (SVM), Relative Vector Machines (RVM), Naïve Bayes, neural network, or Linear Discriminant Analysis (LDA) to thereby generate a fused score image.

In another embodiment, the instructions cause the processor to detect glare in each of the first sample image and the second sample image and to not classify the portions of the first sample image and the second sample image that are identified as glare.

In another embodiment, the instructions cause the processor to normalize the intensities of the first sample image and the second sample image.

In another embodiment, the first sample image is selected from the group consisting of UV, RGB, Vis-NIR, SWIR, Raman, NIR-eSWIR, and eSWIR, and the second sample image is selected from the group consisting of UV, RGB, Vis-NIR, SWIR, Raman, NIR-eSWIR, and eSWIR.

In another embodiment, the first sample image is RGB, and the second sample image is Vis-NIR.

In another embodiment, the first sample image is RGB and the processor converts the first sample image from RGB to Hue, Saturation, Value (HSV) and the processor omits the Value dimension of the first sample image.

In another embodiment, the second sample image is Vis-NIR.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

Figure 1:
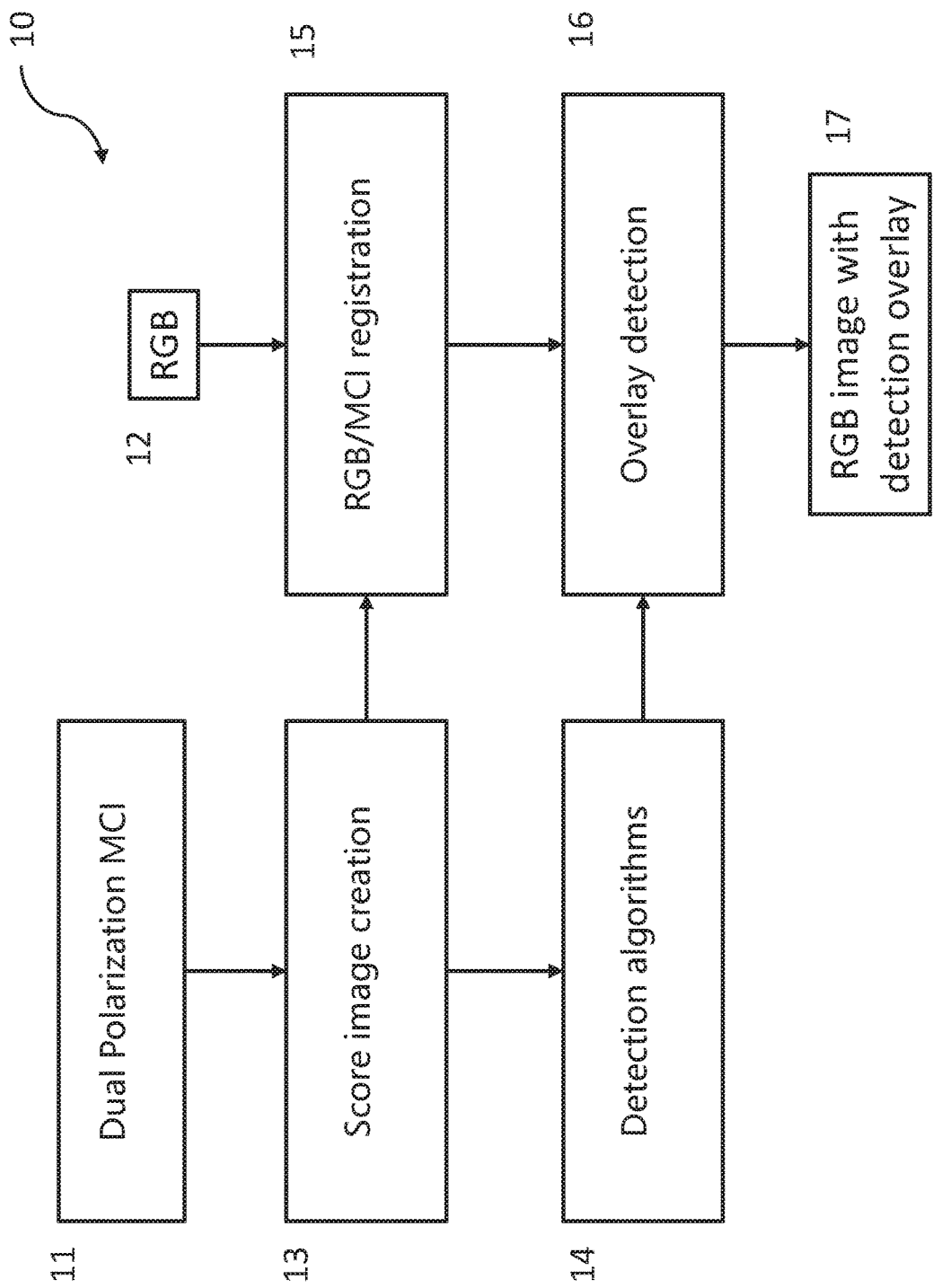
FIG. 1 illustrates one embodiment of detection in real time by registering a RGB image with a MCI image.

This disclosure is not limited to the particular systems, methods, and computer program products described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments described below are not intended to be exhaustive or to limit the teachings to the precise forms disclosed in the following detailed description. Rather, the embodiments are chosen and described so that others skilled in the art may appreciate and understand the principles and practices of the present teachings.

The disclosure contemplates systems, methods, and computer program products that are designed to illuminate a sample with illuminating photons, collect interacted photons from the sample by way of a camera chip, generate two or more sample images from the interacted photons that have been collected and imaged by the camera chip, and fuse the two or more sample images so as to generate a target score image. The target score image is generated by applying mathematical operations to the two or more sample images in order to fuse the two or more sample images. The target score image has greater contrast and information than would be possible with any one of the two or more sample images that are formed from the interacted photons. Further details of the disclosure are provided below.

Illumination Source

The illumination source is not limited and can be any source that is useful in providing the necessary illumination while meeting other ancillary requirements, such as power consumption, emitted spectra, packaging, thermal output, and so forth. In some embodiments, the illumination source is an incandescent lamp, halogen lamp, light emitting diode (LED), quantum cascade laser, quantum dot laser, external cavity laser, chemical laser, solid state laser, organic light emitting diode (OLED), electroluminescent device, fluorescent light, gas discharge lamp, metal halide lamp, xenon arc lamp, induction lamp, or any combination of these illumination sources. In some embodiments, the illumination source is a tunable illumination source, which means that the illumination source is monochromatic and can be selected to be within any desired wavelength range. The selected wavelength of the tunable illumination source is not limited and can be any passband within the ultraviolet (UV), visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wave infrared (MIR), and long-wave infrared (LWIR) ranges.

The above ranges of light correspond to wavelengths of about 180 nm to about 380 nm (UV), about 380 nm to about 720 nm (VIS), about 400 nm to about 1100 nm (VIS-NIR), about 850 nm to about 1800 nm (SWIR), about 1200 nm to about 2450 nm (eSWIR), about 720 nm to about 2500 nm (NIR-eSWIR), about 3000 nm to about 5000 nm (MIR), or about 8000 nm to about 14000 nm (LWIR). The above ranges may be used alone or in combination of any of the listed ranges. Such combinations include adjacent (contiguous) ranges, overlapping ranges, and ranges that do not overlap. The combination of ranges may be achieved by the inclusion of multiple light sources, by filtering light sources, or by the addition of at least one component such as phosphors and/or quantum dots that convert high energy emissions such as UV or blue light into lower energy light having longer wavelengths.

Sample

After the illuminating photons are emitted from the illumination source, they interact with a sample. The sample is not limited and can be any chemical or biological sample where the location of a region of interest is desired to be known versus the sample at large. In some embodiments, the sample is a biological sample and the illuminating photons are used to determine the boundary between a tumor and surrounding non-tumor cells. In some embodiments, the sample is a biological sample and the photons are used to determine the boundary between a tissue experiencing blood restriction and a tissue experiencing blood perfusion. In some embodiments, the sample is a biological structure and the illuminating photons are used to determine a boundary between one biological sample and another biological sample.

Examples of biological samples include ureters, nerves, blood vessels, lymph nodes, healthy organs, organs experiencing blood restriction, organs experiencing blood perfusion, and tumors. In some embodiments, the biological sample is located within a living organism, that is, it is an "in vivo" biological sample. In some embodiments, the sample is not located within a living organism, that is, it is an "in vitro" biological sample. In some embodiments, the illuminating photons are used to distinguish the biological sample from other structures. In some embodiments, the illuminating photons are used to distinguish one biological sample from another biological sample.

Camera Chip

The disclosure contemplates that there is at least one camera chip that collects and images the interacted photons. In some embodiments, the at least one camera chip is characterized by the wavelengths of light that it is capable of imaging. The wavelengths of light that can be imaged by the camera chip are not limited, and include ultraviolet (UV), visible (VIS), near infrared (NIR), visible-near infrared (VIS-NIR), shortwave infrared (SWIR), extended shortwave infrared (eSWIR), near infrared-extended shortwave infrared (NIR-eSWIR). These classifications correspond to wavelengths of about 180 nm to about 380 nm (UV), about 380 nm to about 720 nm (VIS), about 400 nm to about 1100 nm (VIS-NIR), about 850 nm to about 1800 nm (SWIR), about 1200 nm to about 2450 nm (eSWIR), and about 720 nm to about 2500 nm (NIR-eSWIR). The above ranges may be used alone or in combination of any of the listed ranges. Such combinations include adjacent (contiguous) ranges, overlapping ranges, and ranges that do not overlap. The combination of ranges may be achieved by the inclusion of multiple camera chips, each sensitive to a particular range, or a single camera chip that by the inclusion of a color filter array can sense multiple different ranges.

In some embodiments, the at least one camera chip is characterized by the materials from which it is made. The materials of the camera chip are not limited and can be selected based on the wavelength ranges that the camera chip is expected to detect. In such embodiments, the camera chip comprises silicon (Si), germanium (Ge), indium gallium arsenide (InGaAs), platinum silicide (PtSi), mercury cadmium telluride (HgCdTe), indium antimonide (InSb), colloidal quantum dots (CQD), or combinations of any of these.

In some embodiments, the camera chip is provided with a color filter array to produce images. The design of the filter array is not limited. It is to be understood that the term "filter" when used in the context of a camera chip means that the referenced light is allowed to pass through the filter. For example, a "green filter" is a filter that appears green to the human eye by only allowing light having a wavelength of about 520 nm to about 560 nm to pass through the filter, corresponding to the visible color green. A similar "NIR filter" only permits near infrared light (NIR) to pass through. In some embodiments, the filter is a color filter array that is positioned over a camera chip. Such color filter arrays are varied in design but are all related to the original "Bayer" filter color mosaic filters. The color filter array includes BGGR, RGBG, GRGB, RGGB, RGBE, CYYM, CYGM, RGBW (2×2), RGBW (2×2 with diagonal colors), RGBW (2×2 with paired colors), RGBW (2×2 with vertical W), and X-TRANS (sold by Fujifilm Corporation of Tokyo, Japan). The X-TRANS sensor has a large 6×6 pixel pattern that reduces Moiré effect artifacts by including RGB tiles in all horizontal and vertical lines. In the listings, B corresponds to blue, G to green, R to red, E to emerald, C to cyan, Y to yellow, and M to magenta. W corresponds to a "white" or a monochrome tile, which will be further described below.

The W or "white" tile itself includes several configurations. In some embodiments, the W tile does not filter any light, and so all light reaches the camera chip. In those embodiments, the camera chip will detect all of the light within a given range of wavelengths. Depending on the camera chip, this can be UV, VIS, NIR, VIS-NIR, VIS-NIR, VIS-SWIR, or VIS-eSWIR. In some embodiments, the W tile is a filter for VIS, VIS-NIR, NIR, or eSWIR, allowing only VIS, VIS-NIR, NIR, or eSWIR respectively to reach the camera chip. This may be advantageously combined with any of the camera chip materials or electrical structures listed above. Such a filter array can be useful because it enables a single camera chip to detect both visible light and near infrared light and is sometimes referred to as a four-band filter array.

In still further embodiments, the color filter array is omitted and is not provided with the camera chip, which produces a monochromatic image. In such embodiments, the generated image is based solely on the band gap of the materials that make up the camera chip. In other embodiments, a filter is still applied to the camera chip, but only as a monolithic, single filter. For example, the application of a red filter means that the camera chip generates monochromatic images representative of red spectrum. In some embodiments, multiple camera chips, each with a different monolithic, single filter camera chip are employed. As an example, a VIS image can be produced by combining three camera chips having R, G, and B filters, respectively. In another example, a VIS-NIR image can be produced by combining four camera chips having R, G, B, and NIR filters, respectively. In another example, a VIS-eSWIR image can be produced by combining four camera chips having R, G, B, and eSWIR filters, respectively.

In some embodiments, the color array is omitted, and the camera chip utilizes vertically stacked photodiodes organized into a pixel grid. Each of the stacked photodiodes responds to the desired wavelengths of light. For example, a stacked photodiode camera chip includes R, G, and B layers to form a VIS image. In another embodiment, the stacked photodiode camera chip includes R, G, B, and NIR layers to form a VIS-NIR image. In another embodiment, the stacked photodiode camera chip includes R, G, B, and eSWIR layers to form a VIS-eSWIR image.

Image Generation Steps

The disclosure contemplates that a first image is generated by various imaging techniques in a first image generation step. In the first image generation step, photons are generated by one or more illumination sources described above, and the photons travel to the sample. When the photons reach the sample, the photons interact with the sample. The resultant first interacted photons are thereby emitted from the sample and travel to at least one camera chip. The camera chip thereby generates a first image, which is communicated to a processor.

Similarly, the disclosure also contemplates that a second image is generated by various imaging techniques in a second image generation step. In the second image generation step, photons are generated by one or more illumination sources described above, and the photons travel to the sample. When the photons reach the sample, the photons interact with the sample. The resulting second interacted photons are thereby emitted from the sample and travel to at least one camera chip. The at least camera chip thereby generates a second image, which is communicated to an image processor.

The generated image is not limited and can represent at least one image of the wavelengths of UV, RGB, Vis-NIR, SWIR, Raman, NIR-eSWIR, or eSWIR. As used herein, the above ranges of light correspond to wavelengths of about 180 nm to about 380 nm (UV), about 380 nm to about 720 nm (VIS), about 400 nm to about 1100 nm (VIS-NIR), about 850 nm to about 1800 nm (SWIR), about 1200 nm to about 2450 nm (eSWIR), and about 720 nm to about 2500 nm (NIR-eSWIR). In one embodiment, the first image is a RGB image and the second image is a Vis-NIR image.

The image generation techniques are not limited, and in addition to the above discussion, the image generation includes one or more of laser induced breakdown spectroscopy (LIBS), stimulated Raman spectroscopy, coherent anti-Stokes Raman spectroscopy (CARS), elastic scattering, photoacoustic imaging, intrinsic fluorescence imaging, labeled fluorescence imaging, and ultrasonic imaging.

Image Fusion

Two or more images, which include at least first and second images that are generated by the interaction of the above photons with a sample, are fused by an image processor. As mentioned above, the images are not limited and there can be more than two images that are generated. In one embodiment, the first image is a RGB image and the second image is a Vis-NIR ratiometric image. However, these are not the only possibilities, and image fusion can be performed with any two images of the wavelength ranges UV, RGB, Vis-NIR, SWIR, Raman, NIR-eSWIR, or eSWIR, the wavelengths of which are described throughout this disclosure. Such combinations can be used to generate ratiometric images based on the above wavelengths.

In one embodiment of image fusion, a score image is first created, followed by detection or segmentation. To create the score image, RGB and Vis-NIR images are combined using mathematical algorithms to create a score image. The score image shows contrast for the target. For example, in some embodiments, the target will appear as a bright "highlight" while the background will appear as a dark "shadow." The mathematical algorithm that is used for image fusion is not limited, and the algorithm includes Image Weighted Bayesian Fusion (IWBF), Partial Least Squares Discriminant Analysis (PLS-DA), linear regression, logistic regression, Support Vector Machines (SVM), Relative Vector Machines (RVM), Naïve Bayes, Linear Discriminant Analysis (LDA), and neural networks.

When the mathematical algorithm is IWBF, a weighting constant modulates the probability image from respective sensors, and the overall target probability is estimated with different combinations of image cross terms. When detecting multiple target types with the IWBF algorithm, each sensor modality has a single weighting constant for each target type. The selection of each weighting constant for each sensor modality can be achieved by various techniques. Such techniques include Monte Carlo methods, Receiver Operating Characteristic (ROC) curves, linear regression, neural networks, fuzzy logic, Naïve Bayes, Dempster-Shafer theory, and combinations of the above.

The weighting of each sensor modality for a single target type is represented by the following formula:

$$P_{Target}=((1-A) \times W+AP_{T_{S1}}) \times ((1-B) \times W+BP_{T_{1S}}) \times \ldots \times ((1-C) \times W+CP_{T_{Sn}}) \quad \text{Formula 1}$$

The weighting of each sensor modality for multiple target types is represented by the following formulas:

$$P_{T1}=((1-A) \times W+AP_{T_{1S1}}) \times ((1-B) \times W+BP_{T_{1S2}}) \times \ldots \times ((1-C) \times W+CP_{T_{1Sn}}) \quad \text{Formula 2:}$$

$$P_{T2}=((1-D) \times W+DP_{T_{2S1}}) \times ((1-E) \times W+EP_{T_{2S2}}) \times \ldots \times ((1-F) \times W+FP_{T_{2Sn}}) \quad \text{Formula 3:}$$

$$P_{T3}=((1-G) \times W+GP_{T_{3S1}}) \times ((1-H) \times W+HP_{T_{3S2}}) \times \ldots \times ((1-I) \times W+IP_{T_{3Sn}}) \quad \text{Formula 4:}$$

$$P_{Target}=((1-J) \times W+JP_{T1}) \times ((1-K) \times W+KP_{T2}) \times \ldots \times ((1-L) \times W+LP_{T3}) \quad \text{Formula 5:}$$

In the above Formulas 1-5, the Target Type is denoted by T, sensor type by S, number of sensors by n, white image (grayscale consisting only of 1's) by W, detection probability for each target is $P_{T1}$, $P_{T2}$, and $P_{T3}$, and the weights for combining the images are the variables A, B, C, D, E, F, G, H, I, J, K, and L.

The resulting fusion score image or probability image shows enhanced contrast for the target in which a higher pixel intensity corresponds to higher likelihood that the pixel belongs to the target. Similarly, a low pixel intensity corresponds to a low likelihood that the pixel belongs to the target. Detection algorithms utilizing various computer vision and machine learning methods, such as adaptive thresholding and active contours, are applied to the fusion score image to detect the target and find the boundary of the target.

In some embodiments, a score image is not generated using the above equations. Instead, detection or segmentation algorithms are utilized with all N images. Such techniques require multispectral methods where multiple images are assembled into a hypercube. The hypercube has N images and can include any combination of one or more of UV, RGB, Vis-NIR, SWIR, Raman, NIR-eSWIR, or eSWIR. In such embodiments, a score image is not generated. Instead, segmentation algorithms use all N images and thereby identify the target. The multispectral methods are not particularly limited. In some embodiments, the multispectral methods are spectral clustering methods that include one or more of k-means and mean shift methods. In other embodiments, the multispectral detection or segmentation method is a texture based method that groups pixels together based on similar textures measured across spectral bands using Haralick texture features.

In some embodiments, the image fusion in generated from images from two cameras. In other embodiments, the image fusion is generated from three cameras. In embodiments where three cameras are used to generate the image fusion, the first camera generates a first tuning state which forms a first molecular chemical image, the second camera generates a second tuning state which forms a second molecular image, and the third camera generates a RGB image.

In some embodiments where two or more camera chips are included, a stereoscopic image is generated based on the images from each of the two or more camera chips. Stereoscopic images are useful because they permit a viewer to perceive depth in the image, which increases accuracy and realism of the perception. For example, during surgery or other similar activities that are performed with endoscopes, stereoscopic images are useful for manipulating instruments and performing tasks, with greater safety and accuracy than with monoscopic endoscopes. This is because monoscopic endoscopes, having only one camera chip position, cannot provide depth perception. In some embodiments, the stereoscopic image is formed by at least two camera chips and where the camera chips are the same. In some embodiments, the stereoscopic image is formed by at least two camera chips where the camera chips are different. In either of the above embodiments, the camera chips may have the same color filter array, or they may have a different color filter array. In some embodiments, the stereoscopic image is formed by two camera chips that are different, with only one camera chip being provided a color filter array, and the other camera chip being provided either a monochromatic filter or no filter array at all. Anytime that there is more than one camera chip provided, a stereoscopic image can be generated by using the output of each camera chip and combining or fusing the output of each camera chip.

In certain embodiments, the illumination in one of the images is not uniform. This frequently occurs in RGB images, and can cause problems when the image is fused with other images. To avoid these problems the image is converted from RGB color space to HSV (Hue, Saturation, Value) color space. From the HSV image, only the H (Hue) and S (Saturation) channels are considered, and the V (Value) is not included. Thus, in accordance with the disclosure, the RGB image can be represented as an HS image, alternatively referred to as HS channels.

As an alternative to the above described combination of Vis-NIR images with RGB, Vis-NIR images can be alternatively fused with HS channels. By this fusion, problems with illumination that is not uniform are avoided and the fused image, which is formed from a first sample image and a second sample image, shows contrast for the target. The weighting the first sample image and the second sample image is performed by one or more of Image Weighted Bayesian Fusion (IWBF), Partial Least Squares Discriminant Analysis (PLS-DA), linear regression, logistic regression, Support Vector Machines (SVM), Relative Vector Machines (RVM), Naïve Bayes, neural network, or Linear Discriminant Analysis (LDA).

In one embodiment, the weighing of the first sample image and the second sample image is performed by PLS-DA for binary classification or multi-class classification of the Vis-NIR images fused with RGB or the Vis-NIR images In one useful embodiment shown by FIG. 1, a useful method 10 for generating an RGB image with a detection overlay 17 is described. First, the sample is imaged in block 11 by a dual polarization MCI device, which is capable of collecting UV, RGB, Vis-NIR, SWIR, Raman, NIR-eSWIR, or eSWIR light and the sample is also imaged in block 12 by a camera chip that can image RGB light. In block 13, a score image is formed, and the combination of the score image and the RGB image is combined for subsequent image registration. In block 14, detection algorithms are applied to the score image, and the output of these detection algorithms is combined in block 16 with the RGB and MCI registration in overlay detection block 15 to thereby generate in block 17 an RGB image that includes a detection overlay.

Figure 2:
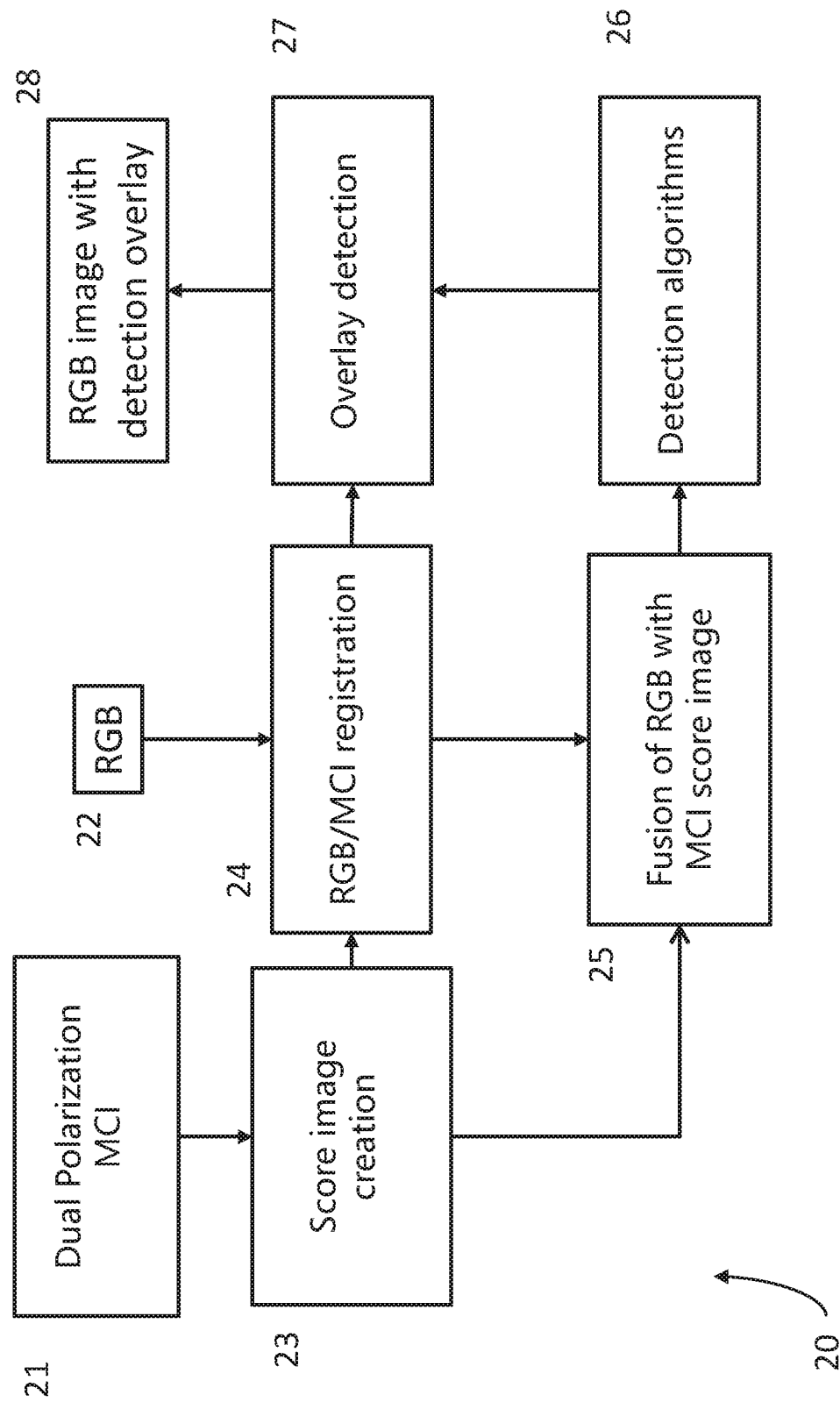
FIG. 2 illustrates another embodiment of detection in real time by fusing a RGB image with a MCI image.

In another useful embodiment shown by FIG. 2, a useful method 20 for generating an RGB image with detection overlay 28 is described. First, the sample is imaged in block 21 by a dual polarization MCI device, which is capable of collecting UV, RGB, Vis-NIR, SWIR, Raman, NIR-eSWIR, or eSWIR light and the sample is also imaged in block 22 by a camera chip that can image RGB light. In block 23, a score image is formed, and the score image is inputted along with the RGB image so that points on the score image can be registered with points in the scene in block 24. The RGB image is also fused with the MCI score image in block 25. With the registration and the score image complete, the fused image which includes information from the MCI score image and the RGB image is inputted to detection algorithms in block 26. With the detection complete, the fused image with detection is inputted to block 27 where it is combined with the registration image from block 24 to thereby form an RBG image with a detection overlay for block 28.

EXAMPLES

Example 1

Testing was performed to generate a fused image. To obtain the fused image, a molecular chemical image was collected, and simultaneously, an RGB image was also collected. Both the molecular chemical image and RGB image collections were performed within the same in vivo surgical procedure. The molecular chemical image was collected using an internally developed MCI endoscope, and a Hopkins® Telescope 0° NIR/ICG φ 10 mm, available from Karl Storz endoscope collected the RGB endoscope collected the RGB image.

Two wavelength images were collected with the MCI endoscope. To fuse the collected MCI and RGB images, the two wavelength images were mathematically combined to produce a ratiometric score image for the target of interest within the in vivo surgical procedure. Next, MCI and RGB images were registered with each other so that each pixel of the MCI image corresponds to the same physical location in the RGB image. The registration was achieved using a hybrid approach that combines features-based and intensity-based methods. The feature-based method is initially applied to estimate geometric transformation between MCI and RGB images. This is achieved by matching the KAZE features. KAZE is a multiscale two-dimensional feature detector and descriptor. An intensity-based method based on similarity metric and optimizer is used to refine the results of the feature-based method. The registration is accomplished by aligning the MCI image to the RGB image using the estimated geometric transformation.

Next, pre-processing is performed. First, a glare mask is generated by detecting glare in each of the MCI and RGB images. Pixels identified as glare are not classified. Second, the MCI and RGB images are normalized so that the intensities of the pixels from the two images are on an equal range and the intensity does not influence the contribution of each image modality to the fused image.

After pre-processing is performed, the fusion is performed. Using labeled data that was generated by a prior training step, the classifier detects pixels belonging to the target of interest. To perform the fusion, three (3) frames of RGB image and a MCI ratiometric score image are input into the classifier. In the Example, IWBF is the method used to find optimal weights for the images that minimize prediction error on the training set. Weights determined by IWBF on the training set are applied to the images and the weighted images are thereby mathematically combined to create the fused score image. The final fused score image is then displayed and shows increased contrast for the target compared to the background. This increased contrast allows for improved detection performance of the target from the background. In some embodiments, detection algorithms that use computer vision and machine learning methods are applied to the fused score image to locate or determine a final detection of the target. The final detection is overlaid onto the RGB image. The final detection overlaid onto the RGB image is particularly useful for when a user desires to locate a feature that would otherwise be difficult to identify. In one embodiment, the user is a surgeon that desires to have improved visualization of an organ.

Example 2

Additional testing was performed to generate fused images employing PLS-DA for binary classification or multi-class classification. First, RGB images and a VIS-NIR images are generated from a sample. Specifically, 8 images were generated and the RGB images were registered to data from nerve complex scenes. The RGB images were converted to HSV, with the Value (brightness) portion of the image omitted in order to avoid uneven illumination in the images. Next, three dimensional hypercubes were generated. The first dimension of the hypercube was hue data, the second dimension of the hypercube was saturation data, and the third dimension of the hypercube was the spectral wavelength. In this Example, the spectral wavelengths are 500 nm and 580 nm, which correspond to a nerve recipe.

The hypercubes were collected for scenes that included the tissue types of bowel, fat, muscle, and nerve, and a PLS-DA was applied to discriminate the different tissues from each other. Table 1 shows the results of this when applied to bowel, fat, muscle, and nerve. Any events where the PLS-DA concluded that the tissue was other than the tissue in the scene was denoted a misclassification. For example, in the first row of Table 1, of six total scenes, five correctly identified bowel tissue in a bowel sample, while one scene identified fat tissue in a bowel sample, resulting in a misclassification rate of 16.7%. As shown in Table 1, even when multiple classes must be distinguished, the misclassification rate has an average of 7.1%.

TABLE 1

|         | Bowel | Fat | Muscle | Nerve | Misclassification Rate (%) |
|---------|-------|-----|--------|-------|----------------------------|
| Bowel   | 5     | 1   | 0      | 0     | 16.7                       |
| Fat     | 1     | 7   | 0      | 0     | 12.5                       |
| Muscle  | 0     | 0   | 6      | 0     | 0                          |
| Nerve   | 0     | 0   | 0      | 8     | 0                          |
| Average |       |     |        |       | 7.1                        |

Similar to the preceding experiment, additional hypercubes were collected for scenes that included the tissue types of bowel, fat, muscle, nerve, and ureter, and a PLS-DA was applied to discriminate the different tissues from each other. Table 2 shows the results of this when applied to bowel, fat, muscle, nerve, and ureter. As shown in Table 2, the inclusion of the ureter did not degrade 2 class performance, which maintained 100% accuracy.

TABLE 2

|         | Bowel | Fat | Muscle | Nerve | Ureter | Misclassification Rate (%) |
|---------|-------|-----|--------|-------|--------|----------------------------|
| Bowel   | 4     | 0   | 0      | 0     | 2      | 33.3                       |
| Fat     | 0     | 7   | 0      | 0     | 1      | 12.5                       |
| Muscle  | 0     | 0   | 6      | 0     | 0      | 0                          |
| Nerve   | 1     | 0   | 0      | 7     | 0      | 12.5                       |
| Ureter  | 2     | 3   | 0      | 0     | 1      | 83.3                       |
| Average |       |     |        |       |        | 26.5                       |

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A method of fusing images, the method comprising:
    illuminating a sample with illuminating photons;
    obtaining a first sample image from interacted photons that have interacted with the sample and have traveled to a first camera chip;
    obtaining a second sample image from interacted photons that have interacted with the sample and have traveled to a second camera chip; and
    fusing the first sample image and the second sample image by weighting the first sample image and the second sample image, wherein the weighting of the first sample image and the second sample image is performed by one or more of Image Weighted Bayesian Fusion (IWBF), Partial Least Squares Discriminant Analysis (PLS-DA), linear regression, logistic regression, Support Vector Machines (SVM), Relative Vector Machines (RVM), Naïve Bayes, or Linear Discriminant Analysis (LDA), to thereby generate a fused score image,
    wherein the second sample image is a molecular chemical image, and
    wherein the second sample image is obtained by a dual polarization device.

2. The method of claim 1, further comprising detecting glare in each of the first sample image and the second sample image and not classifying the portions of the first sample image and the second sample image that are identified as glare.

3. The method of claim 1, further comprising normalizing the intensities of the first sample image and the second sample image.

4. The method of claim 1, wherein the first sample image is selected from the group consisting of UV, RGB, Vis-NIR, SWIR, Raman, NIR-eSWIR, and eSWIR, and the second sample image is selected from the group consisting of UV, RGB, Vis-NIR, SWIR, Raman, NIR-eSWIR, and eSWIR.

5. The method of claim 4, wherein the first sample image is RGB, and the second sample image is Vis-NIR.

6. The method of claim 1, wherein the first sample image is RGB that is converted to Hue, Saturation, Value (HSV) and the Value dimension of the first sample image is omitted.

7. The method of claim 6, wherein the second sample image is Vis-NIR.

8. A system for fusing images, the system comprising:
    an illumination source configured to illuminate a sample with illuminating photons;
    a first camera chip configured to obtain a first sample image from interacted photons that have interacted with the sample;
    a second camera chip configured to obtain a second sample image from interacted photons that have interacted with the sample; and
    a processor that during operation fuses the first sample image and the second sample image by weighting the first sample image and the second sample image, wherein the weighting of the first sample image and the second sample image is performed by one or more of Image Weighted Bayesian Fusion (IWBF), Partial Least Squares Discriminant Analysis (PLS-DA), linear regression, logistic regression, Support Vector Machines (SVM), Relative Vector Machines (RVM), Naïve Bayes, or Linear Discriminant Analysis (LDA) to thereby generate a fused score image,
    wherein the second sample image is a molecular chemical image, and
    wherein the second sample image is obtained by a dual polarization device.

9. The system of claim 8, wherein the processor detects glare in each of the first sample image and the second sample image and does not classify the portions of the first sample image and the second sample image that are identified as glare.

10. The system of claim 8, wherein the processor normalizes the intensities of the first sample image and the second sample image.

11. The system of claim 8, wherein the first sample image is selected from the group consisting of UV, RGB, Vis-NIR, SWIR, Raman, NIR-eSWIR, and eSWIR, and the second sample image is selected from the group consisting of UV, RGB, Vis-NIR, SWIR, Raman, NIR-eSWIR, and eSWIR.

12. The system of claim 11, wherein the first sample image is RGB, and the second sample image is Vis-NIR.

13. The system of claim 8, wherein the first sample image is RGB and the processor converts the first sample image from RGB to Hue, Saturation, Value (HSV) and the processor omits the Value dimension of the first sample image.

14. The system of claim 13, wherein the second sample image is Vis-NIR.

15. A computer program product for fusing images embodied by instructions on a non-transitory computer readable storage medium, which when the instructions are executed by a processor causes:
    an illumination source to illuminate a sample with illuminating photons;

a first camera chip to obtain a first sample image from interacted photons that have interacted with the sample;

a second camera chip to obtain a second sample image from interacted photons that have interacted with the sample; and the processor to fuse the first sample image and the second sample image by weighting the first sample image and the second sample image, wherein the weighting of the first sample image and the second sample image is performed by one or more of Image Weighted Bayesian Fusion (IWBF), Partial Least Squares Discriminant Analysis (PLS-DA), linear regression, logistic regression, Support Vector Machines (SVM), Relative Vector Machines (RVM), Naïve Bayes, or Linear Discriminant Analysis (LDA) to thereby generate a fused score image, wherein the second sample image is a molecular chemical image, and wherein the second sample image is obtained by a dual polarization device.

16. The computer program product of claim 15, wherein the instructions cause the processor to detect glare in each of the first sample image and the second sample image and to not classify the portions of the first sample image and the second sample image that are identified as glare.

17. The computer program product of claim 15, wherein the instructions cause the processor to normalize the intensities of the first sample image and the second sample image.

18. The computer program product of claim 15, wherein the first sample image is selected from the group consisting of UV, RGB, Vis-NIR, SWIR, Raman, NIR-eSWIR, and eSWIR, and the second sample image is selected from the group consisting of UV, RGB, Vis-NIR, SWIR, Raman, NIR-eSWIR, and eSWIR.

19. The computer program product of claim 18, wherein the first sample image is RGB, and the second sample image is Vis-NIR.

20. The computer program product of claim 15, wherein the first sample image is RGB and the processor converts the first sample image from RGB to Hue, Saturation, Value (HSV) and the processor omits the Value dimension of the first sample image.

21. The computer program product of claim 20, wherein the second sample image is Vis-NIR.

22. The method of claim 1, further comprising applying a detection algorithm that uses one or more of computer vision and machine learning to the fused score image.

23. The system of claim 8, wherein the processor further applies a detection algorithm that uses one or more of computer vision and machine learning to the fused score image.

24. The computer program product of claim 15, wherein the instructions cause the processor to further apply a detection algorithm that uses one or more of computer vision and machine learning to the fused score image.

* * * * *